(12) United States Patent
Ben-Mokhtar et al.

(10) Patent No.: US 8,021,395 B2
(45) Date of Patent: Sep. 20, 2011

(54) INTERSPINOUS VERTEBRAL IMPLANT

(75) Inventors: Mourad Ben-Mokhtar, Geneva (CH); Jean-Marc Fuentes, Montpellier (FR)

(73) Assignee: Eden Spine, LLC, Lake Mary, FL (US)

( * ) Notice: Subject to any disclaimer, the term of this patent is extended or adjusted under 35 U.S.C. 154(b) by 663 days.

(21) Appl. No.: 12/124,801

(22) Filed: May 21, 2008

(65) Prior Publication Data
US 2009/0005819 A1   Jan. 1, 2009

(30) Foreign Application Priority Data

May 22, 2007 (EP) .................................. 07010112

(51) Int. Cl.
*A61B 17/70* (2006.01)
*A61F 2/44* (2006.01)

(52) U.S. Cl. ............ 606/249; 606/248; 623/17.11
(58) Field of Classification Search .......... 606/246–250, 606/279; 623/17.11–17.16
See application file for complete search history.

(56) References Cited

U.S. PATENT DOCUMENTS

| | | | |
|---|---|---|---|
| 5,704,937 A | 1/1998 | Martin | |
| 5,733,284 A * | 3/1998 | Martin | 606/248 |
| 5,797,910 A | 8/1998 | Martin | |
| 6,626,944 B1 * | 9/2003 | Taylor | 623/17.16 |
| 6,761,720 B1 * | 7/2004 | Senegas | 606/249 |
| 7,163,558 B2 * | 1/2007 | Senegas et al. | 623/17.11 |
| 7,837,688 B2 * | 11/2010 | Boyer et al. | 606/86 A |
| 7,854,752 B2 * | 12/2010 | Colleran et al. | 606/279 |
| 2002/0143331 A1 | 10/2002 | Zucherman et al. | |
| 2005/0049708 A1 | 3/2005 | Atkinson et al. | |
| 2006/0036240 A1 | 2/2006 | Colleran et al. | |

* cited by examiner

*Primary Examiner* — Pedro Philogene
(74) *Attorney, Agent, or Firm* — Curatolo Sidoti Co., LPA; Salvatore A. Sidoti; Peter R. Detone

(57) ABSTRACT

According to certain embodiments, disclosed is a vertebral interspinous implant including first and second supports (2,3) defining in their center part respective fixation bodies (7,8) to accept spinal processes of two respective vertebrae, these fixation bodies being located in a same sagittal plane, first and second elastically compressible bodies (4) being set between the first and second supports (2,3) and on each side of the said sagittal plane (P), first and second rigid guides (10) around which are arranged, respectively, the first and second elastically compressible bodies (4), each of these guides (10) optionally being connected at one of its extremities to the supports (2,3) and including at, at least, one of its extremities an abutment (13) adapted to cooperate with an abutment (14) of the corresponding support (3) in order to limit the separation of the supports (2,3) in the direction of the spine.

36 Claims, 6 Drawing Sheets

INTERSPINOUS VERTEBRAL IMPLANT

CROSS REFERENCE TO RELATED APPLICATIONS

This application claims priority of the filing date of European Patent Application No. 07010112.6, filed May 22, 2007, which is hereby incorporated by reference.

TECHNICAL FIELD

Disclosed is an interspinous vertebral implant, meaning an implant intended to be inserted between the spinal processes of two adjacent vertebrae, in order to function as a stabilizer and notably relieve the inter-vertebral disk.

BACKGROUND

It is known through U.S. Patent Application Publication No. 2002/0143331, FIG. 9, of an interspinous vertebral implant including first and second supports defining fixation bodies to respective adjacent spinal processes and in between which is placed, an elastic body of annular shape and coaxial with the supports. The elastic body is placed between the bottom of an annular cavity of the first support and an annular male body of the second support which is axially guided in this cavity. The peripheral wall of the first support includes an internal annular protuberance which can cooperate with an annular shoulder of the male body of the second support in order to limit the gaps of the supports. The face of the extremity of the peripheral wall of the first support constitutes also a stop which can cooperate with an edge of the second support in order to limit the compression of the elastic body.

According to U.S. Patent Application Publication No. 2002/0143331, this implant presents several disadvantages. At first instance, it can be noted that this implant and its elastic body have a circular shape. To obtain a certain capacity of shock absorption, the elastic body must have sufficient dimensions. Yet if the diameter of the implant is increased, its overloading in the antero-posterior direction will be too great and will necessitate the damaging, in too great of a measure, of the vertebral tissues for the setting in place of the implant. On another hand, the presence of the annular male body of the second support and of the peripheral wall of the first support limit in great fashion, the space available for the elastic body. Another disadvantage is that the stops which limit the gaps of the supports appear undersized in order to really resist to physiological loads.

FR Patent Application No. 2 774 581, diagram 4, describes an interspinous vertebral implant consisting of first and second supports defining in their center part respective fixation bodies for spinal processes of two respective vertebrae, these fixation bodies being located in the same sagittal plane, and first and second elastically compressible bodies in the direction of the spine, these elastically compressible bodies being put in place between the first and second supports and on both sides of the aforementioned sagittal plane.

The elastically compressible bodies are in the shape of bellows defining waterproof inner walls filled with a liquid and a core made in a viscoelastic material. This implant according to FR 2 774 581 seems to present a greater capacity of shock absorption than the one described in the document U.S. Patent Application Publication No. 2002/0143331. However, this implant appears to be difficult to achieve because its extremities of the bellows must be solidly fastened to the supports in order to maintain the inner walls waterproofed and to avoid the separation of the supports from one another. Yet, FR 2 774 581 does not explain how to fasten the bellows to the supports. This problem of bellows' fixation to the supports is that much more critical, given that the implant does neither comprise any stops to limit the supports gap nor to limit the bellows' compression. It is important to also note that the viscoelastic cores are not really guided and therefore susceptible to move laterally, which can unbalance the implant and perturb the functioning of the bellows.

SUMMARY

The present implant aims to remedy to the aforementioned disadvantages of the state of the art and discloses An interspinous vertebral implant comprising at least two supports defining in their center part respective fixation bodies to accept spinal processes of two respective vertebrae, said fixation bodies being located in the same plane of symmetry; at least two elastic bodies that are elastically compressible in the direction of the spine, said elastically compressible bodies being arranged between said supports and on each side of said plane; at least two rigid guides engaged with said supports, wherein at least one of its extremities comprises an abutment to cooperate with an abutment of the corresponding support to limit the separation of said at least two supports in the direction of the spine.

According to certain illustrative embodiments, the interspinous vertebral implant comprises at least first and second supports defining in their center part respective fixation bodies to accept spinal processes of two respective vertebrae, said fixation bodies being located in the same sagittal plane; at least first and second elastic bodies that are elastically compressible in the direction of the spine, said elastically compressible bodies being arranged between said supports and on each side of said sagittal plane; at least first and second rigid guides being engaged with said supports, wherein at one of its extremities comprises an abutment to cooperate with an abutment of the corresponding support to limit the separation of said supports in the direction of the spine.

According to certain illustrative embodiments, the interspinous vertebral implant comprises first and second supports defining in their center part respective fixation bodies to accept spinal processes of two respective vertebrae, said fixation bodies being located in the same sagittal plane; first and second elastic bodies that are elastically compressible in the direction of the spine, said elastically compressible bodies being arranged between said first and second supports and on each side of said sagittal plane; first and second rigid guides around which are arranged, respectively, said first and second elastically compressible bodies, each of said first and second guides being connected at one of its extremities to one of said supports and at least one of its extremities comprising an abutment to cooperate with an abutment of the corresponding support to limit the separation of said first and second supports in the direction of the spine.

Thus, the rigid bodies insure, both, a function of guidance and a function of stop. This design allows the elastic bodies will stay properly in place within the implant and to give a great sturdiness to the stops. The implant can present a light overload in the antero-posterior direction, which can allow, notably, to keep a good portion of the natural ligaments. The overload of the implant in the lateral direction is a bit impeding since the corresponding tissues are mostly made up of muscle.

Also disclosed is an implant comprising at least two supports defining in their center part respective fixation bodies to accept portions of adjacent bones, said fixation bodies being located in the same anatomical plane; at least two elastically compressible bodies arranged between said supports and on each side of said anatomical plane; and at least two rigid guides engaged at its extremities to said supports and at least one of its extremities comprising an abutment to cooperate with an abutment of the corresponding support to limit the separation of said supports.

According to certain illustrative embodiments, the implant comprises at least first and second supports defining in their center part respective fixation bodies to accept portions of adjacent bones, said fixation bodies being located in the same sagittal plane; at least first and second elastically compressible bodies arranged between said supports and on each side of said sagittal plane; and at least first and second rigid guides being engaged with said supports, wherein at one of its extremities comprises an abutment to cooperate with an abutment of the corresponding support to limit the separation of said supports.

According to further illustrative embodiments, the implant comprises first and second supports defining in their center part respective fixation bodies to accept a portions of adjacent bones, said fixation bodies being located in the same sagittal plane; first and second elastically compressible bodies arranged between said supports and on each side of said sagittal plane; first and second rigid guides around which are arranged said elastically compressible bodies, each of said guides being connected at one of its extremities to said supports and at least one of its extremities comprising an abutment to cooperate with an abutment of the corresponding support to limit the separation of said first and second supports.

Additionally disclosed is a method of implanting an interspinous vertebral implant having at least one elastically compressible body into a space between two adjacent vertebrae comprising resecting at least a portion of either one or both of ligament and soft tissue to expose said space; and inserting the interspinous vertebral implant having at least one preloaded elastically compressible body under compression into the space between the two adjacent vertebrae.

Some illustrative embodiments of the presently disclosed interspinous vertebral implant are described hereinafter and defined in the dependant claims.

Other characteristics and advantages of the presently disclosed interspinous vertebral implant will be evident by the reading of the following detailed description of several illustrative embodiments of the interspinous vertebral implant made in reference to the annexed drawing figures.

DETAILED DESCRIPTION

Figure 1:
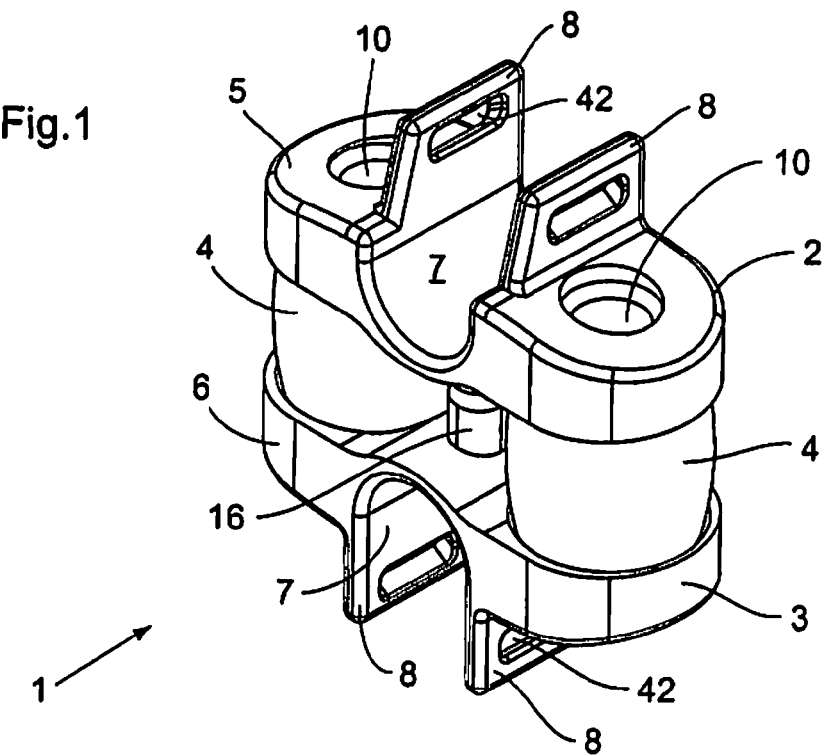
FIGS. 1 and 2 are respectively a perspective view and a frontal cross-section view of an interspinous vertebral implant according to a first illustrative embodiment.
Figure 2:
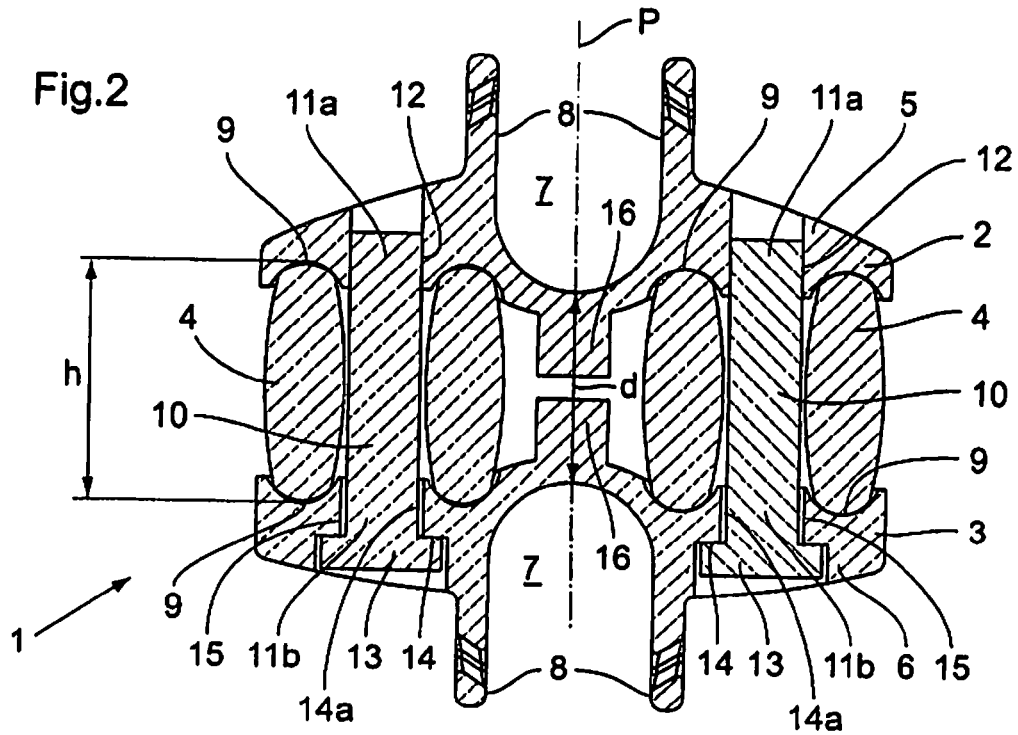

In reference to diagrams FIGS. 1 and 2, an interspinous vertebral implant 1 according to a first illustrative embodiment, comprises a superior support 2, an inferior support 3 and two elastic bodies 4 interposed between the supports 2,3. Each support 2,3 comprises a plate 5,6 elongated in the lateral direction and in the central part of which, is intended a hollow out 7 in the shape of a U spreading out in the antero-posterior direction. The lateral walls of the hollow out 7 are extended by a pair of fins 8 which protrudes on the exterior surface of the plate 5,6. The pair of fins 8 forms with the hollow out 7, a fixation body to accept a spinous process. More precisely, the hollow out 7 and the space between the fins 8 are intended to receive a spinal process, the maintaining of spinal process in the body 7, 8 being insured, for example, by one or some synthetic ligaments as it will be explained further in relation with the FIG. 8. The respective fixation bodies 7,8 of the supports 2,3 are located in a same sagittal plane (P), which constitutes a plan of symmetry for the implant 1. Each support 2,3 with its plate 5,6 and its fins 8, is typically a single-block part made of a bio-compatible material, metallic for example, of a greater hardness than this of the elastic bodies 4.

The elastic bodies 4 are aligned in the lateral direction and located on each side of the sagittal plane of symmetry (P). The elastic bodies 4 are elastically compressible in the direction of the spine (vertical direction P on FIG. 2) and are typically made in a visco-elastic matter such as, without limitation, silicone. The elastic bodies 4 have a general cylindrical, annular shape, and their extremities rest, without being fastened through another mean, in annular grooves 9 made inside the interior faces in regard to the plates 5, 6. Each elastic body 4 surrounds a rigid guiding rod 10, typically metallic, which extends parallely to the plane (P), in the direction of the spine, and which is connected at one or both its extremities to the plates 5,6 of the supports 2,3, respectively. Each of guiding rods 10 may be shaped like a screw, having a threaded extremity 11a, which is screwed inside a corresponding tapped bore 12 of the plate 5 of the superior support 2 and of which the head 13 rests against an annular shoulder 14 in a crossing bore 15 of the plate 6 of the inferior support 3 inside which runs the other extremity 11b of the screw's rod. Each guiding rod 10 is free in regard to the wall of the corresponding bore 15, in a fashion that the support 3 is axially mobile, that is in the direction of the spine, in comparison to the support 2. The guiding rods' 10 head 13 and the shoulders 14 constitute, however, abutments which limit, in a reliable manner, the gap between supports 2, 3 and thus, prevent the latter to separate from one another during the flexion movements of the patient. The elastic bodies 4 are thus, permanently well maintained in place around the guiding rods 10.

According to certain illustrative embodiments, the section of each bore 15 is bigger than the outer diameter of the corresponding guiding rod 10 in order to leave a clearance 14a between the walls of the bores 15 and the guiding rods 10 to allow inclination movements of the supports 2,3 one in comparison to the other in the frontal plane (lateral flexion movements of the patient) or in the sagittal plane (flexion/extension movements of the patient) as well as axial rotation movements of the supports 2,3 one in comparison to the other (torsion), all these movements having a limited amplitude through the walls of the bores 15.

According to certain illustrative embodiments, the guiding rods 10 are screwed in a manner, to sufficiently bring nearer the supports 2,3 so that the elastic bodies 4 be in a pre-strained or pre-loaded state before the installation of the implant. Such pre-strain allows the implant to withstand loads up to a certain threshold without added compression of the elastic bodies 4. It is notably possible to choose the pre-strained state in such a fashion that once the implant is put in place, it can be able to withstand the loads exercised by the spine, when the patient is in the erect position, without added compression of the elastic bodies 4. This guarantees the efficient maintaining of the spinal processes' gap.

According to alternative embodiments, the guiding rods' 10 extremities 11a could be fastened in the support 2 in another manner other than by screwing, for example, without limitation, by driving out, bonding or welding. By the term "fastened" one means a fixation which maintains axially the immobile extremities 11a in comparison to the support 2 during the movements relative of the supports 2,3.

In addition, the implant 1 comprises, according to certain illustrative embodiments, two blocks 16 which protrude facing each other on the interior respective faces of the plates 5,6, in the center part of the implant 1, between the elastic bodies 4. These blocks 16 can act as an abutment or stop, against one another during extension movements of the patient to limit the compression of the elastic bodies 4 and thus protect these latter.

As one can see on FIG. 2, the space between the elastic bodies 4 can be used to bring nearer the fixation body 7,8 from the superior support 2 to the fixation body 7,8 of the inferior support 3. In fact, a disadvantage of the traditional interspinous implants is, that they need to perform a resection of a part of the spinous process to clear a sufficient space allow insertion of the implant. Such a resection, in addition to its tedious character, can entail a weakness and then a rupture of the spinous processes. With the presently disclosed implant, such a resection is not necessary, or can be performed in a minimal manner, in view of the hollow outs 7 to accept the spinal processes which are made in the plates 5,6 and which are near each other. According to certain embodiments, the distance d between the respective bottoms of hollow outs 7 is substantially equal, even inferior at times, to the height h of the elastic bodies 4. Thus, the implant can be installed in place without resection of the spinal processes while comprising elastic bodies 4 of great height and of great shock absorbing capacity.

Figure 3:
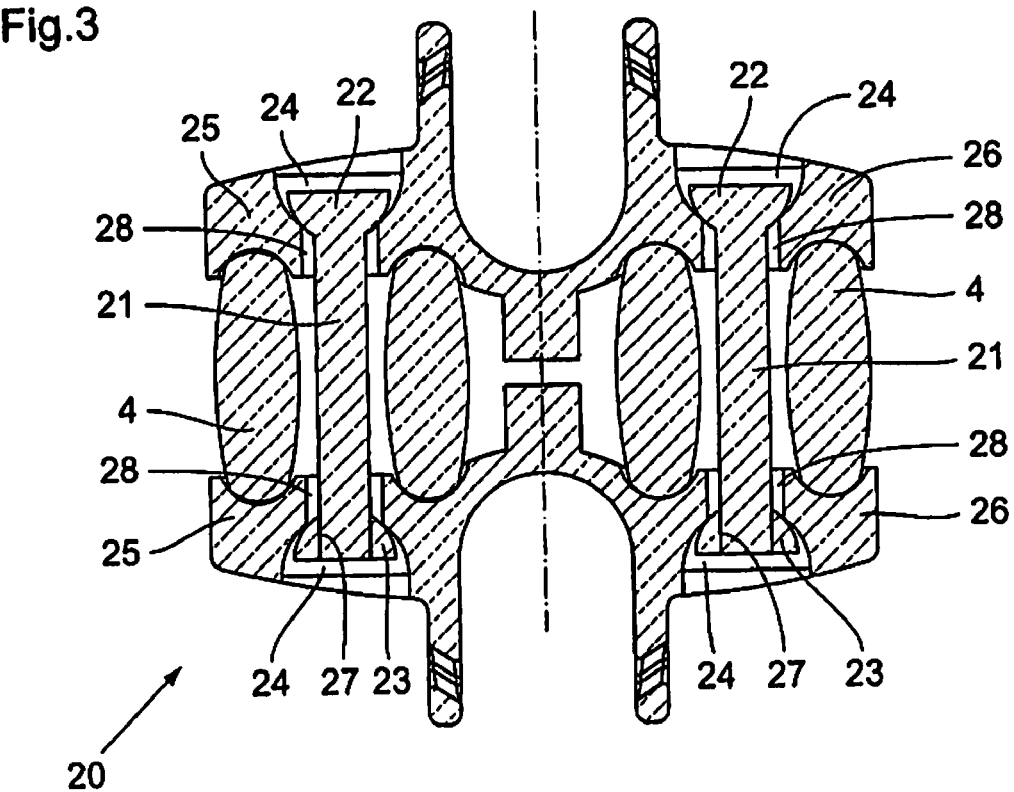
FIGS. 3 and 4 are frontal cross section views of an interspinous vertebral implant according to a second illustrative embodiment, respectively in a straight up position and in an inclined position.
Figure 4:
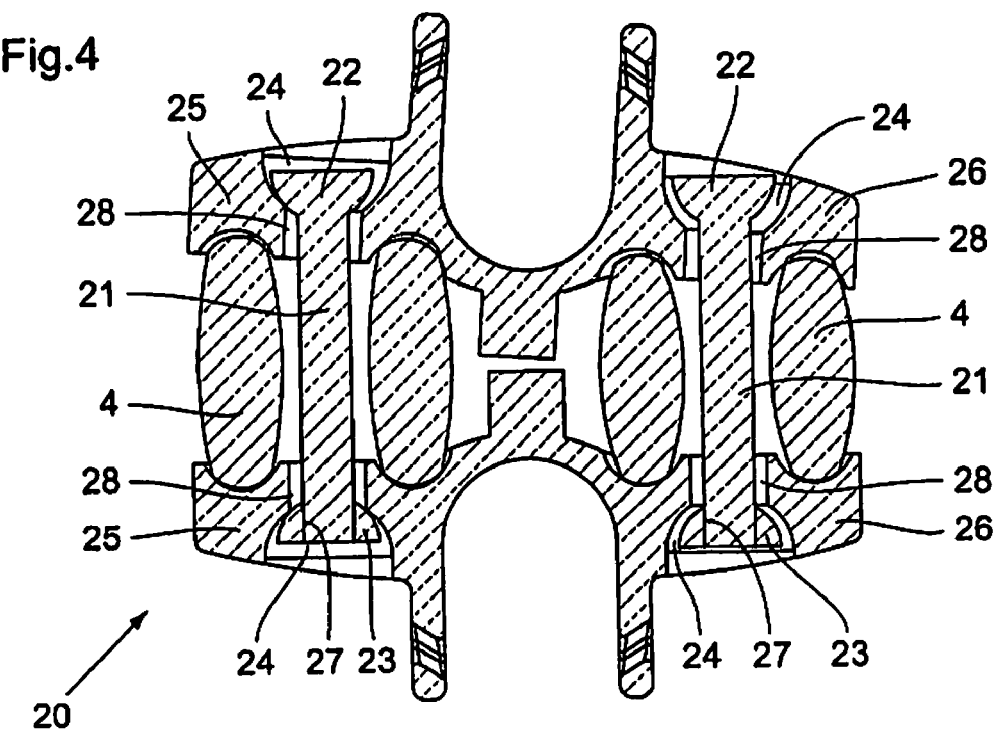

FIGS. 3 and 4 show an interspinous vertebral implant 20 according to a second illustrative embodiment of the invention. This implant 20 differs from the implant 1 according to the first embodiment of the implant, because the guiding rods 21 are not fastened in one of the plate but have at each their extremities a hemispherical shaped head 22, 23. These hemispherical shaped heads 22,23 rest in hemispherical shaped casing 24, but of a bigger radius formed in the plates 25 of the supports 26. Thus, guides 21 are merely engaged with the supports, but not fixedly connected or otherwise fastened to the supports. Both heads 22,23 of each guiding rods 21 play the role of stops to limit the gap of the supports 26. At least, one of these heads, 22,23 is a screw nut 23 which cooperate with a threading 27 of the rod 21 to regulate the gap of the supports 26 and thus the pre-straining of the elastic bodies 4. Clearances 28 are made between the guiding rods 21 and the walls of the plates' bores 25, in which the rods 21 run to permit to supports 26 to incline itself, one in comparison to the other, in the frontal plane during a lateral flexion movement of the patient (as shown on FIG. 4) or in the sagittal plane during a flexion/extension movement of the patient or to axially rotate, one in comparison to the other, during a torsion movement of the patient. The spherical shape of the heads 22,23 and of the casings 24 facilitate the mentioned inclination movements.

Figure 5:
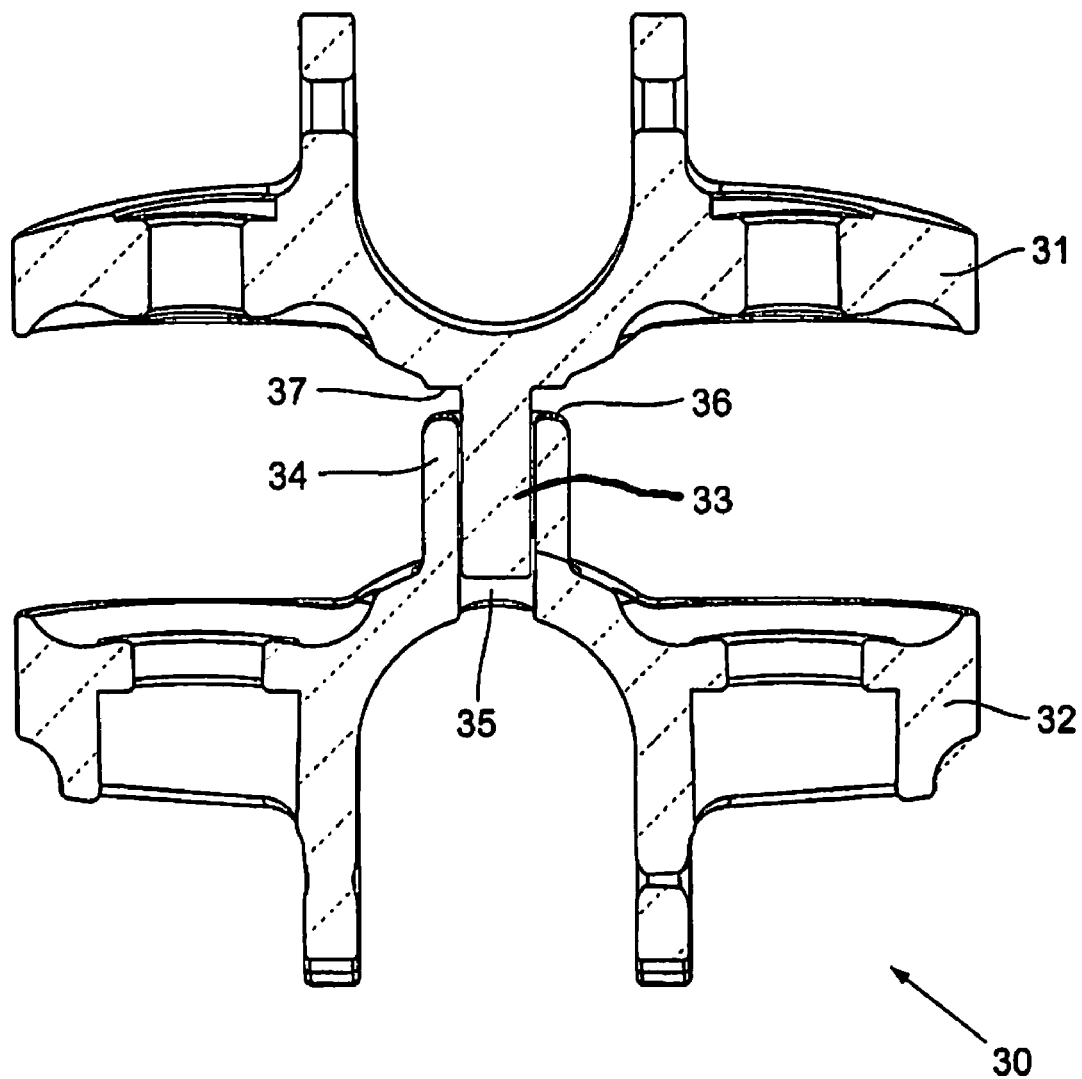
FIG. 5 is a frontal cross section view of an interspinous vertebral implant according to a third illustrative embodiment.
Figure 6:
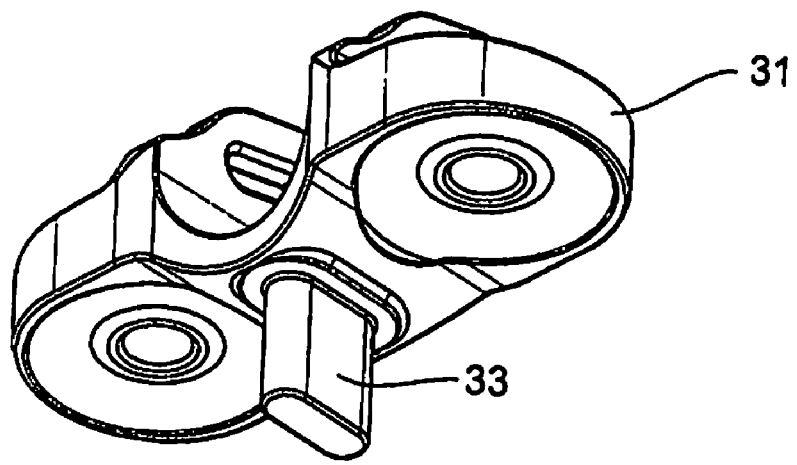
FIGS. 6 and 7 are perspective views, respectively, of a male part support and a female part support of the interspinous vertebral implant according to the third illustrative embodiment.
Figure 7:
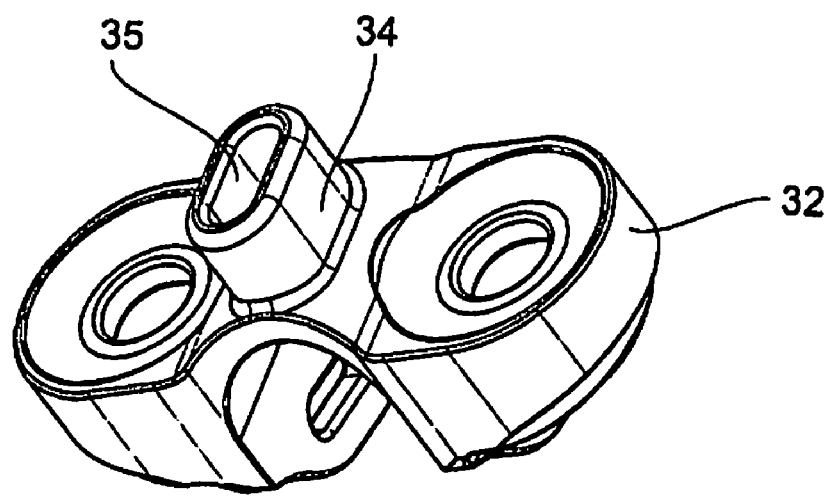

FIGS. 5 to 7 show an interspinous inter-vertebral implant 30 according to a third illustrative embodiment. The implant 30 comprises two supports 31, 32 of a similar or same type as the supports 2,3 of the first illustrative embodiment of the implant, or the supports 26 of the second illustrative embodiment of the implant, the guiding rods (not shown) of the similar or same type as the rods 10 of the first illustrative embodiment or the rods 21 of the second illustrative embodiment, and elastic bodies (not shown) of similar or the same type as the elastic bodies 4 of the first and second illustrative embodiments. In the place of simple stop blocks 16, the implant 30 comprises, in its center part located between the elastic bodies, an assembly of a male part 33 which bulges from the interior face of the support's plate 31 and of a female part 34 which bulges from the interior face of the other support's plate 32. The female part 34 comprises a bore 35 in which slides the male 33 during the relative axial moves of the supports 31, 32. A surface of extremity 36 of the female part 34 can abut or otherwise bump into or against the resting surface 37 of the support 31 surrounding the base of the male part 33 during extension movements of the patient to limit the compression of the elastic bodies and thus protect the latter. The section of the bore 35 is bigger than the male part's section to allow relative inclination movements, in the frontal plane and in the sagittal plane, of the supports 31, 32 in determined limits. The male part 33 and the bore 35 have, both, a non-circular shaped section, oblong that is, in the illustrative example shown, in order to limit the relative axial rotation movements of the supports 31, 32. The clearance between the male 33 and female 34 parts is smaller than the one between the guiding rods and the supports 31, 32. Thus, it is the assembly 33, 34, that limits the relative inclination and axial rotation movements of supports 31, 32. This set up allows protection of the guiding rods.

Also disclosed is a method of implanting the interspinous vertebral implant having at least one elastically compressible body into a space between two adjacent vertebrae within the spine. The method involves removal of at least portions of certain ligaments and soft tissue to expose or otherwise gain access to the target implant site. According to certain embodiments, at least a portion of the interspinous ligament and soft tissue are resected to expose the target implant site. In some instances, it may be necessary or beneficial to also resect at least a portion of the supraspinous ligament as well. Once the target implant site has been prepared by resection of the necessary ligaments and soft tissue, the interspinous vertebral implant is inserted into the target implant site.

The pre-loaded interspinous vertebral implant is implanted under compression into the target site between two adjacent vertebrae. This is generally accomplished by implanting an interspinous vertebral implant having at least one elastically compressible body which permits the implant to be implanted under compression. Illustrative implants 1, 20 and 30 disclosed herein each comprises at least one elastically compressible body and are able to be implanted under compression into the target site between two adjacent vertebrae. Implanting the interspinous vertebral implant into the target implant site under compression avoids having to cut or otherwise resect bony portions of the spinous processes of the adjacent vertebrae.

The interspinous vertebral implant may be implanted under compression with an appropriate surgical instrument or tool. The surgical instrument engages the interspinous vertebral implant and maintains the desired level of compression during the implantation into the target site. Because the implant is implanted under compression, the implant is maintained in proper position and the risk of implant migration is minimized or avoided.

The method of implanting the interspinous vertebral implant includes securing the interspinous vertebral implant to the superior and inferior spinous processes of the two adjacent vertebrae. Securing the implant to the spinous processes generally includes securing by means of at least one synthetic ligament. According to certain embodiments, the implant is secured to the spinous processes by means of two synthetic ligaments. An illustrative method for securing the implant to the spinous processes is described in further detail below with reference to FIG. 8. The method of implanting the interspinous vertebral implant may also include rejoining ends of the resected supraspinous ligament.

Figure 8:
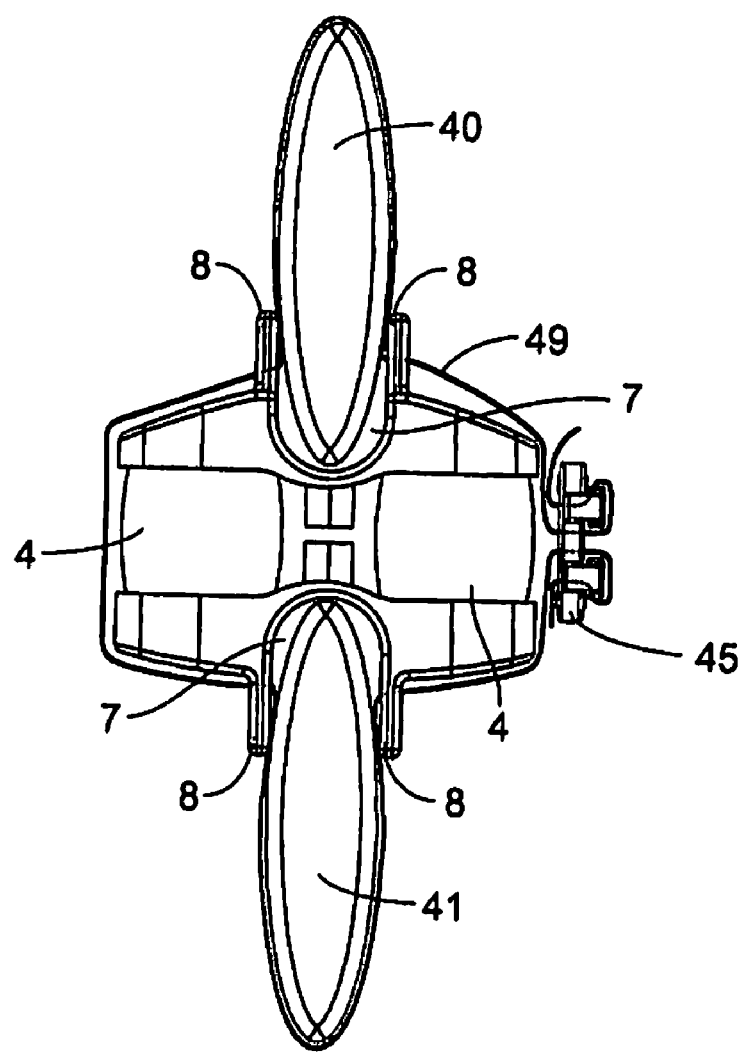
FIG. 8 is a frontal plane view showing an implant according to an illustrative embodiment in place between two the spinal processes.

FIG. 8 demonstrates how, according to the disclosure, the implant can be installed in place. As shown in FIG. 8, the implant represented is one of the illustrative implants 1 or 20. It could, however, be the implant 30. The implant is placed between two consecutive spinal processes 40, 41 if need be by compressing the elastic bodies 4 in order to facilitate the insertion of the implant and then in releasing the compression effort once the implant in place. The fins 8 each comprise a hole 42 (see FIG. 1) which extends in the antero-posterior direction. These holes 42 allow the passage of one or several synthetic ligaments used to maintain, in a smooth manner, the spinal processes 40, 41 in the fixation bodies 7,8. Depending on the pre-strained state of the elastic bodies 4, these synthetic ligaments are more or less solicited during flexion movements of the patient. Through their elasticity, these synthetic ligaments allow a vertebral gap even when the gap of the supports 2, 3, respectively 26, is blocked by the stops 13, 14, respectively 22, 23, 24. However, this gap of the vertebrae stays within physiological limits.

Figure 9:
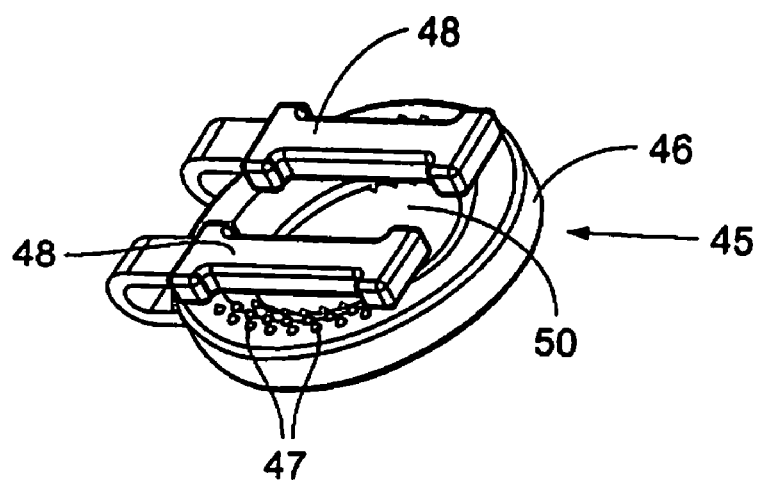
FIGS. 9 and 10 are respectively a perspective view and a profile view of a stopping part used to stop a ligament serving to maintain the implant between two spinal processes.
Figure 10:
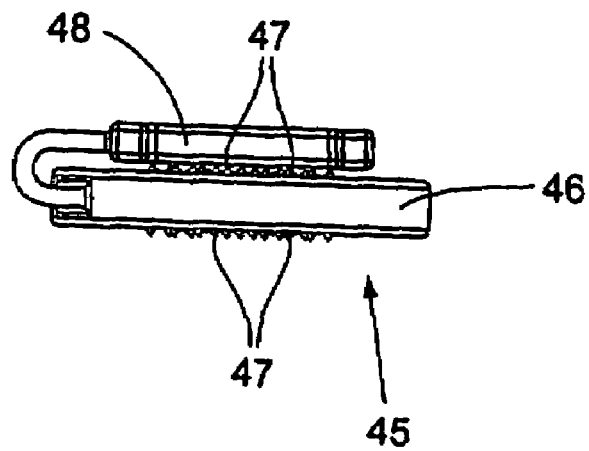
Figure 11:
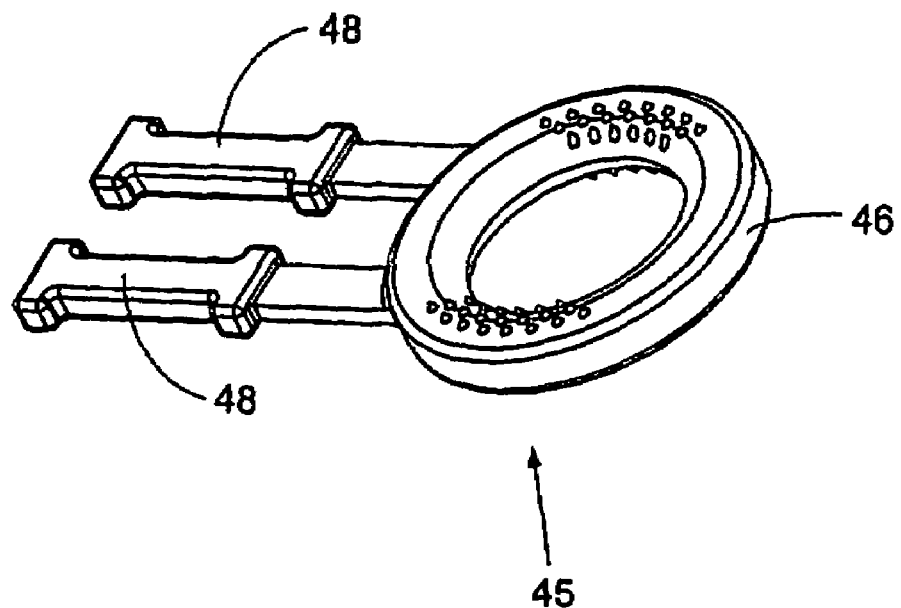
FIG. 11 is a perspective view of the stopping part in a non-folded intermediary state.

Traditionally, such synthetic ligaments are stopped and gathered to each other with knots. According to a characteristic of the process of installation of the implant, a part 45 is used to stop and gather the end parts of a ligament without knotting. This part is shown on FIGS. 9 and 10. It comprises an annular part 46 consisting of small wedges 47 on its superior and inferior surfaces, and two parallel strips 48 attached at one of their extremities to the external peripheral surface of the annular part 46 and brought back over the annular part 46 by a 180° folding. FIG. 11 shows the stopping part 45 before the folding of the strips 48.

As represented FIG. 8, the stopping part 45 is placed freely near the implant with its inferior face turned toward the implant. A synthetic ligament 49 goes around the implant, sensibly in the frontal plan passing through the holes 42 of the fins 8 and by going around the superior spinal a process 40 through its superior extremity and the inferior spinal process 41 through its inferior extremity. Both ends of the ligaments 49 pass through the center part of the hole 50 of the annular part 46 through the inferior face of the latter, then form a ring around the strips 48 respectively to cross again the hole 50 in its peripheral part. The extremities of the ligament 49 are left free. While pulling on its extremities, the surgeon may hold tight on the ligament 49 in the stopping part 45. The small wedges 47 cooperate then with the ligament 49 to insure a good maintaining of this latter.

The described interspinous vertebral implant experiences no pre-loading at the neutral points in flexion, extension, lateral bending and axial rotation and therefore permits a balanced and controlled range of motion.

According to certain embodiments, provided is an implant for insertion between two adjacent bones. The implant comprises at least two supports defining in their center part respective fixation bodies to accept a portions of adjacent bones and being located in the same anatomical plane, at least two elastically compressible bodies arranged between the supports and on each side of the anatomical plane, and at least two rigid guides enegaged with the supports. According to certain embodiment, the elastically compressible bodies are arranged or otherwise disposed around the rigid guides. Depending on the embodiment, each of the guides may be connected at one of its extremities to the supports and at least one of its extremities comprising an abutment to cooperate with an abutment of the corresponding support to limit the space between the supports.

The implant may comprise first and second supports defining in their center part respective fixation bodies to accept a portions of adjacent bones and being located in the same anatomical plane, first and second elastically compressible bodies arranged between the first and second supports and on each side of the anatomical plane and first and second rigid guides. The elastically compressible bodies may be arranged or otherwise disposed around the rigid guides. Each of the rigid guides may be connected at one of its extremities to the supports and at least one of its extremities comprising an abutment to cooperate with an abutment of the corresponding support to limit the space between the first and second supports.

The abutments of the guides of the implant maintain the elastically compressible bodies in a preloaded state. The implant also includes a clearance between each guide and at least one of said first and second supports to allow relative inclination and axial rotation movement of the supports.

According to certain embodiments, the supports define in a central zone, located between elastically compressible bodies, a female part comprising a bore and a male part to slide axially in the bore with a clearance allowing relative inclination movements of supports. The male part section and the bore section have a non-circular shape to limit relative axial rotation movements of supports, and the clearance is smaller than the clearance between the guide and the supports such that the relative inclination and axial rotation movements are limited by the assembly of male and female parts and not by the assembly of the guide and supports.

The guides of the implant may be fastened at one of their extremities in one of supports and have an abutment at the other extremity. According to other embodiments, at least one of the extremities of each of at least one of the guides has a spherical shape favoring an inclination of supports, one in comparison to the other.

The supports of the implant may also further define respective stops located between the elastically compressible bodies and being able to come in contact with each other, to limit the compression of the elastically compressible bodies.

The supports may be in the shape of plates intended to be placed between spinal processes and having said fixation bodies. The fixation bodies each define a casing that is intended to receive a portion of a bone. The distance (d) between the respective bottoms of the casings is substantially equal to the height (h) of the elastically compressible bodies, or the distance (d) may be inferior to the height (h).

While the interspinous vertebral implant and process for implanting the same have been described in connection with various illustrative embodiments, it is to be understood that other similar embodiments may be used or modifications and additions may be made to the described embodiments for performing the same function disclosed herein without deviating therefrom. The embodiments described above are not necessarily in the alternative, as various embodiments may be combined to provide the desired characteristics. Therefore, the implant and process for implanting the same should not be limited to any single embodiment, but rather construed in breadth and scope in accordance with the recitation of the appended claims.

The invention claimed is:

1. An interspinous vertebral implant comprising:
   at least two supports defining in their center part respective fixation bodies to accept spinal processes of two respective vertebrae, said fixation bodies being located in the same plane of symmetry;
   at least two elastic bodies that are elastically compressible in the direction of the spine, said elastically compressible bodies being arranged between said supports and on each side of said plane; and
   at least two rigid guides engaged with said supports, wherein at least one of its extremities comprises an abutment to cooperate with an abutment of the corresponding support to limit the separation of said at least two supports in the direction of the spine.

2. An interspinous vertebral implant comprising:
   at least first and second supports defining in their center part respective fixation bodies to accept spinal processes of two respective vertebrae, said fixation bodies being located in the same sagittal plane;
   at least first and second elastic bodies that are elastically compressible in the direction of the spine, said elastically compressible bodies being arranged between said supports and on each side of said sagittal plane;
   at least first and second rigid guides being engaged with said supports, wherein at one of its extremities comprises an abutment to cooperate with an abutment of the corresponding support to limit the separation of said supports in the direction of the spine.

3. The interspinous vertebral implant of claim 2, comprising:
   first and second supports defining in their center part respective fixation bodies to accept spinal processes of two respective vertebrae, said fixation bodies being located in the same sagittal plane;
   first and second elastic bodies that are elastically compressible in the direction of the spine, said elastically compressible bodies being arranged between said first and second supports and on each side of said sagittal plane;
   first and second rigid guides around which are arranged, respectively, said first and second elastically compressible bodies, each of said first and second guides being connected at one of its extremities to one of said supports and at least one of its extremities comprising an abutment to cooperate with an abutment of the corresponding support to limit the separation of said first and second supports in the direction of the spine.

4. The interspinous vertebral implant according to claim 2 or 3, wherein said abutments of said guides maintain the elastically compressible bodies in a pre-loaded state.

5. The interspinous vertebral implant according to claim 4, wherein said elastically compressible bodies are made of a visco-elastic material.

6. The interspinous vertebral implant according to claim 2 or 3, wherein said implant comprises a clearance between each guide and at least one of said first and second supports to allow relative inclination and axial rotation movement of said first and second supports.

7. The interspinous vertebral implant according to claim 6, wherein said supports respectively, define in a central zone, located between said elastically compressible bodies, a female part comprising a bore and a male part assembled to slide axially in the bore with a clearance allowing relative inclination movements of supports, the male part and the bore having a non-circular shape to limit relative axial rotation movements of supports, said clearance being smaller than the clearance between the guide and the supports such that said relative inclination and axial rotation movements are limited by the assembly of male and female parts and not by the assembly of the guide and supports.

8. The interspinous vertebral implant according to claim 2 or 3, wherein said guide are fastened at one of their extremities in one of supports and have an abutment at the other extremity.

9. The interspinous vertebral implant according to claim 7, wherein said guide are fastened at one of their extremities in one of supports and have an abutment at the other extremity.

10. The interspinous vertebral implant according to claim 6, wherein at least one said extremities of each of said guide has a spherical shape favoring an inclination of supports, one in comparison to the other.

11. The interspinous vertebral implant according to claim 10, wherein at least one said extremities of each of said guide has a spherical shape favoring an inclination of supports, one in comparison to the other.

12. The interspinous vertebral implant according to claim 10, wherein said spherical shaped extremity, or, at least one spherical shaped extremities of each guide comprises a screw nut of spherical shape.

13. The interspinous vertebral implant according to claim 11, wherein said spherical shaped extremity, or, at least one spherical shaped extremities of each guide comprises a screw nut of spherical shape.

14. The interspinous vertebral implant according to claim 2 or 3, wherein said supports further define respective stops located between the elastically compressible bodies and being able to come in contact with each other, to limit the compression of the elastically compressible bodies.

15. The interspinous vertebral implant according to claim 7, wherein said supports further define respective stops located between the elastically compressible bodies and being able to come in contact with each other, to limit the compression of the elastically compressible bodies.

16. The interspinous vertebral implant according to claim 2 or 3, wherein said supports are in the shape of plates intended to be placed between spinal processes and having said fixation bodies.

17. The interspinous vertebral implant according to claim 7, wherein said supports are in the shape of plates intended to be placed between spinal processes and having said fixation bodies.

18. The interspinous vertebral implant according to claim 14, wherein said supports are in the shape of plates intended to be placed between spinal processes and having said fixation bodies.

19. The interspinous vertebral implant according to claim 2 or 3, wherein said fixation bodies each define a casing intended to receive a spinal process.

20. The interspinous vertebral implant according to claim 7, wherein said fixation bodies each define a casing intended to receive a spinal process.

21. The interspinous vertebral implant according to claim 14, wherein said fixation bodies each define a casing intended to receive a spinal process.

22. The interspinous vertebral implant according to claim 16, wherein said fixation bodies each define a casing intended to receive a spinal process.

23. The interspinous vertebral implant according to claim 19, wherein said distance (d) between the respective bottoms of the casings is substantially equal to the height (h) of the elastically compressible bodies.

24. The interspinous vertebral implant according to claim 23, wherein said distance (d) is inferior to said height (h).

25. The interspinous vertebral implant according to claim 2 or 3, wherein each of said fixation bodies comprise fins between which can be received a spinal process, said fins each comprising a hole allowing the passage of a ligament.

26. The interspinous vertebral implant according to claim 7 wherein each of said fixation bodies comprise fins between which can be received a spinal process, said fins each comprising a hole allowing the passage of a ligament.

27. The interspinous vertebral implant according to claim 14, wherein each of said fixation bodies comprise fins between which can be received a spinal process, said fins each comprising a hole allowing the passage of a ligament.

28. The interspinous vertebral implant according to claim 16, wherein each of said fixation bodies comprise fins between which can be received a spinal process, said fins each comprising a hole allowing the passage of a ligament.

29. A device comprising the interspinous vertebral implant according to claim 2 or 3 and a stop part intended to remain free at proximity of said implant and adapted to stop without knotting end parts of a ligament for maintaining of the implant between the spinal processes.

30. The interspinous vertebral implant according to claim 7, wherein each of said fixation bodies comprise fins between which can be received a spinal process, said fins each comprising a hole allowing the passage of a ligament.

31. The interspinous vertebral implant according to claim 14, wherein each of said fixation bodies comprise fins between which can be received a spinal process, said fins each comprising a hole allowing the passage of a ligament.

32. The interspinous vertebral implant according to claim 16, wherein each of said fixation bodies comprise fins between which can be received a spinal process, said fins each comprising a hole allowing the passage of a ligament.

33. The device according claim 29, wherein said stop part comprises an annular part and parallel strips folded back over the annular part.

34. The device according claim 30, wherein said stop part comprises an annular part and parallel strips folded back over the annular part.

35. The device according claim 31, wherein said stop part comprises an annular part and parallel strips folded back over the annular part.

36. The device according claim 32, wherein said stop part comprises an annular part and parallel strips folded back over the annular part.

* * * * *